(12) United States Patent
Larkin

(10) Patent No.: US 9,060,766 B2
(45) Date of Patent: Jun. 23, 2015

(54) SUTURE FIXATION KIT OF PARTS, SYSTEM, AND DEVICE

(76) Inventor: Daniel Larkin, St. Paul, MN (US)

(*) Notice: Subject to any disclaimer, the term of this patent is extended or adjusted under 35 U.S.C. 154(b) by 1087 days.

(21) Appl. No.: 12/197,696

(22) Filed: Aug. 25, 2008

(65) Prior Publication Data

US 2010/0049247 A1 Feb. 25, 2010

(51) Int. Cl.
- *A61B 17/04* (2006.01)
- *A61B 19/02* (2006.01)
- *A61B 17/00* (2006.01)

(52) U.S. Cl.
CPC .......... *A61B 17/0466* (2013.01); *A61B 17/04* (2013.01); *A61B 17/0487* (2013.01); *A61B 19/026* (2013.01); *A61B 2017/00761* (2013.01)

(58) Field of Classification Search
CPC .................. A61B 17/0466; A61B 17/0487
USPC ............... 606/232, 233, 151, 157, 158
See application file for complete search history.

(56) References Cited

U.S. PATENT DOCUMENTS

| | | | |
|---|---|---|---|
| 784,018 A * | 2/1905 | Witherbee | 606/233 |
| 3,212,502 A | 10/1965 | Myers | |
| 3,695,271 A * | 10/1972 | Chodorow | 606/233 |
| 3,931,821 A * | 1/1976 | Kletschka et al. | 606/233 |
| 4,164,046 A | 8/1979 | Cooley | |
| 4,210,148 A * | 7/1980 | Stivala | 606/232 |
| 4,291,698 A | 9/1981 | Fuchs et al. | |
| 4,476,865 A * | 10/1984 | Failla et al. | 606/158 |
| 4,549,545 A | 10/1985 | Levy | |
| 4,823,794 A | 4/1989 | Pierce | |
| 5,059,201 A | 10/1991 | Asnis | |
| 5,084,058 A | 1/1992 | Li | |
| 5,087,263 A | 2/1992 | Li | |
| 5,160,339 A * | 11/1992 | Chen et al. | 606/158 |
| 5,314,433 A | 5/1994 | Li | |
| 5,366,480 A * | 11/1994 | Corriveau et al. | 606/233 |
| 5,403,348 A | 4/1995 | Bonutti | |
| 5,489,288 A | 2/1996 | Buelna | |
| 5,544,664 A | 8/1996 | Benderev et al. | |
| 5,569,250 A * | 10/1996 | Sarver et al. | 606/281 |
| 5,570,700 A | 11/1996 | Vogeler | |
| 5,658,313 A | 8/1997 | Thal | |
| 5,697,950 A | 12/1997 | Fucci et al. | |
| 5,709,708 A | 1/1998 | Thal | |
| 5,720,765 A | 2/1998 | Thal | |
| 5,782,864 A | 7/1998 | Lizardi | |
| 5,810,853 A * | 9/1998 | Yoon | 606/151 |
| 5,879,371 A | 3/1999 | Gardiner et al. | |
| 5,951,590 A | 9/1999 | Goldfarb | |
| 5,961,539 A | 10/1999 | Northrup, III et al. | |
| 5,984,933 A * | 11/1999 | Yoon | 606/148 |
| 6,074,409 A | 6/2000 | Goldfarb | |
| 6,093,201 A * | 7/2000 | Cooper et al. | 606/232 |
| 6,106,545 A | 8/2000 | Egan | |

(Continued)

*Primary Examiner* — Jonathan W Miles
*Assistant Examiner* — Todd J Scherbel
(74) *Attorney, Agent, or Firm* — Dicke, Billig & Czaja, PLLC

(57) ABSTRACT

A suture fixation system that is configured to secure a suture includes a pad and a suture fixation device configured to clamp and retain at least one end of a suture. The pad includes a suture surface opposite a tissue surface and defines an opening formed through the suture and tissue surfaces that is sized to provide a margin around a tissue lesion to be sutured. The suture is employed to stitch the tissue lesion closed, the suture having at least one free end that is held in place by the suture fixation device, and the pad configured to elevate a portion of the suture away from the tissue.

16 Claims, 14 Drawing Sheets

(56) References Cited

U.S. PATENT DOCUMENTS

| | | |
|---|---|---|
| 6,554,852 B1 | 4/2003 | Oberlander |
| 6,706,047 B2 | 3/2004 | Tanner et al. |
| 6,911,034 B2 | 6/2005 | Nobles et al. |
| 7,033,379 B2 * | 4/2006 | Peterson ............... 606/232 |
| 7,163,563 B2 * | 1/2007 | Schwartz et al. ......... 623/23.76 |
| 2006/0207609 A1 * | 9/2006 | Gil et al. ............... 128/849 |
| 2006/0293670 A1 * | 12/2006 | Smisson et al. ............ 606/69 |
| 2008/0208213 A1 * | 8/2008 | Benjamin et al. ........... 606/139 |

* cited by examiner

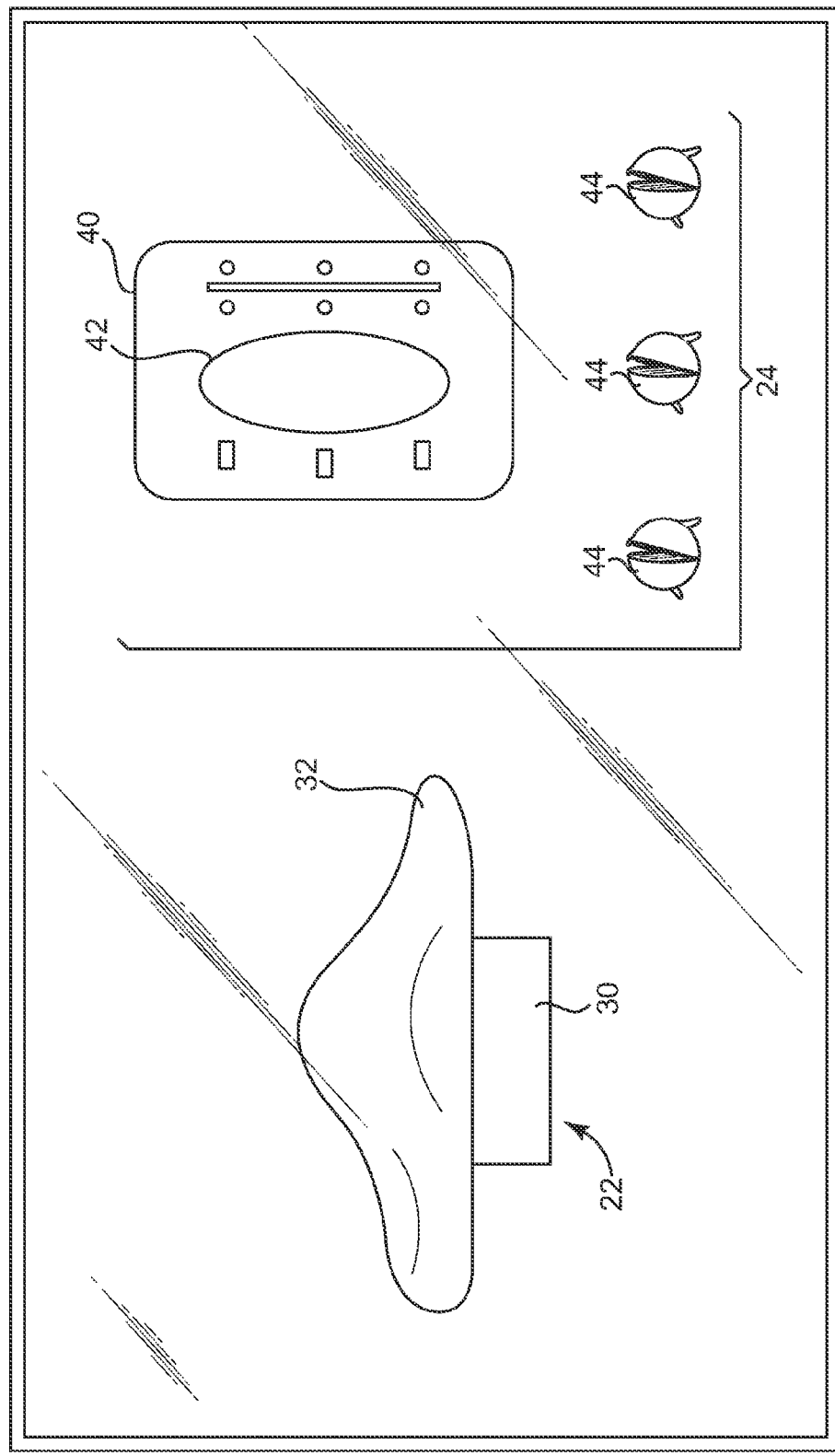

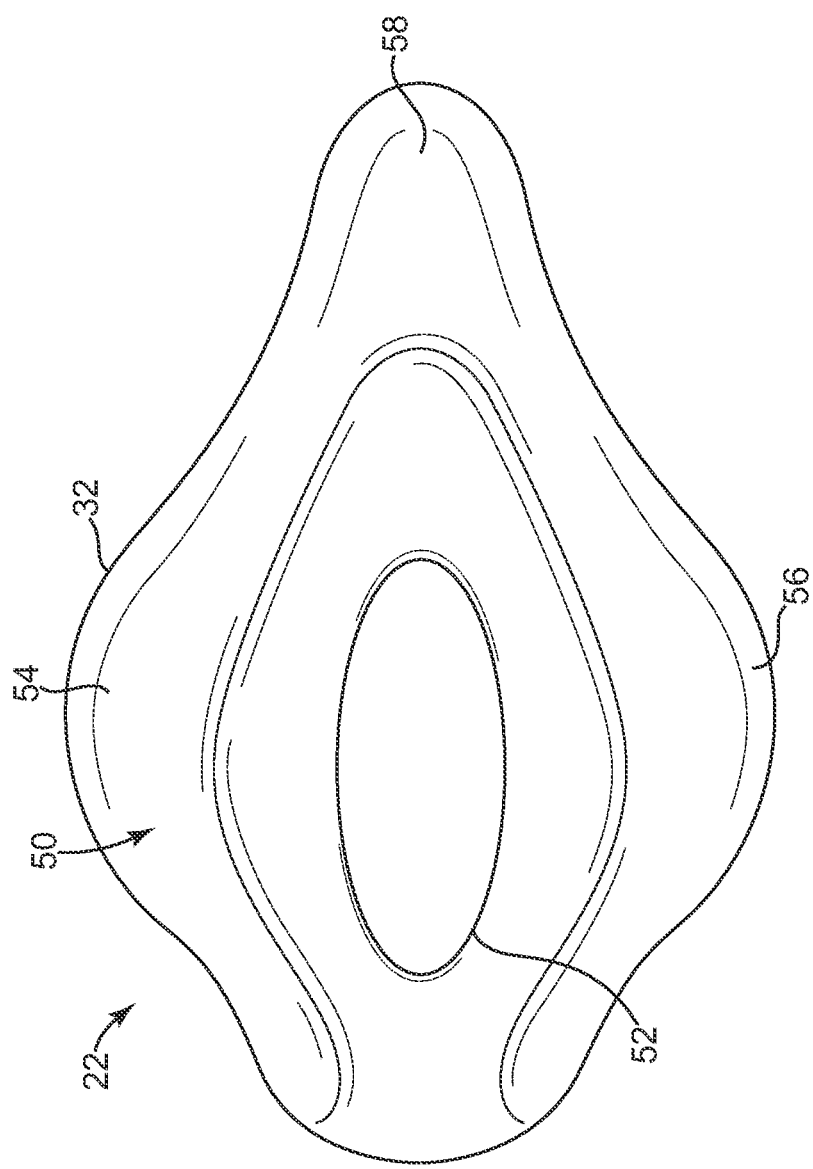

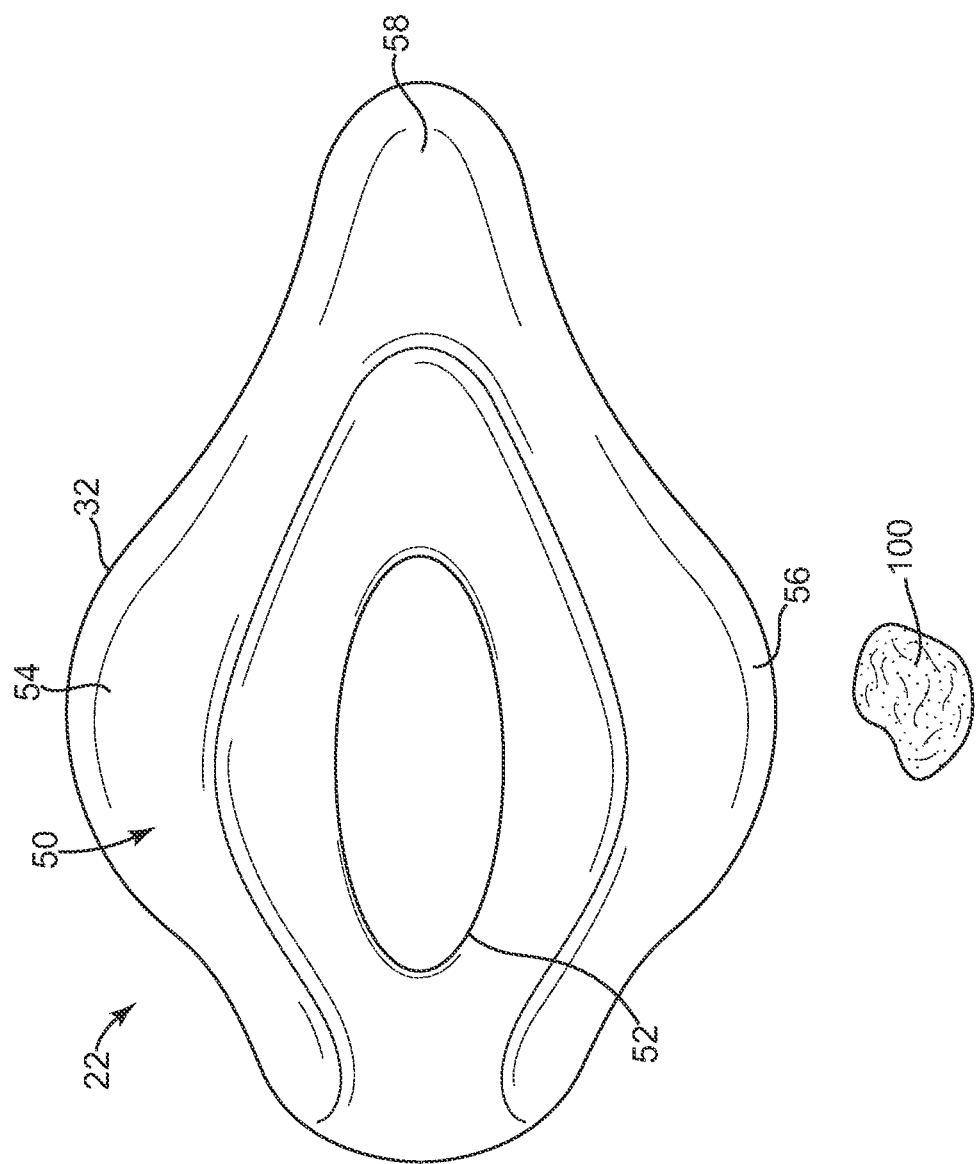

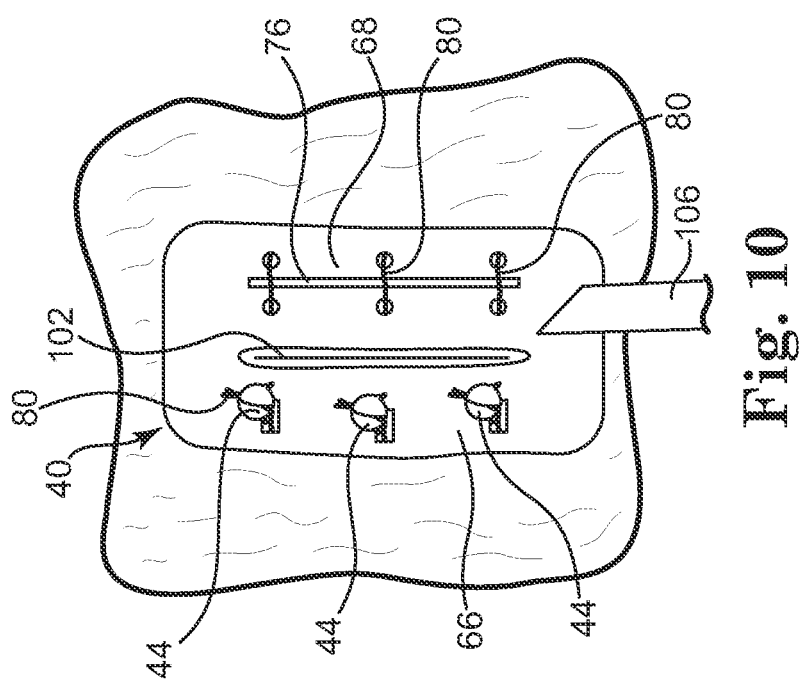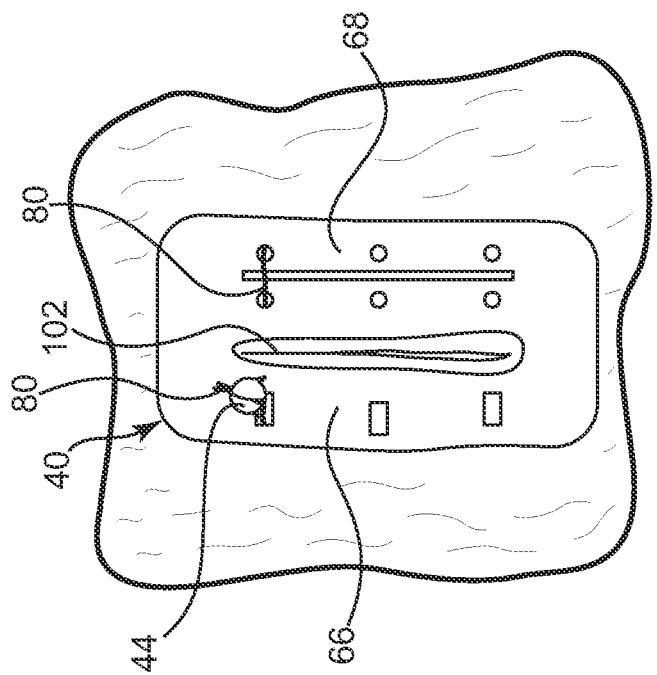

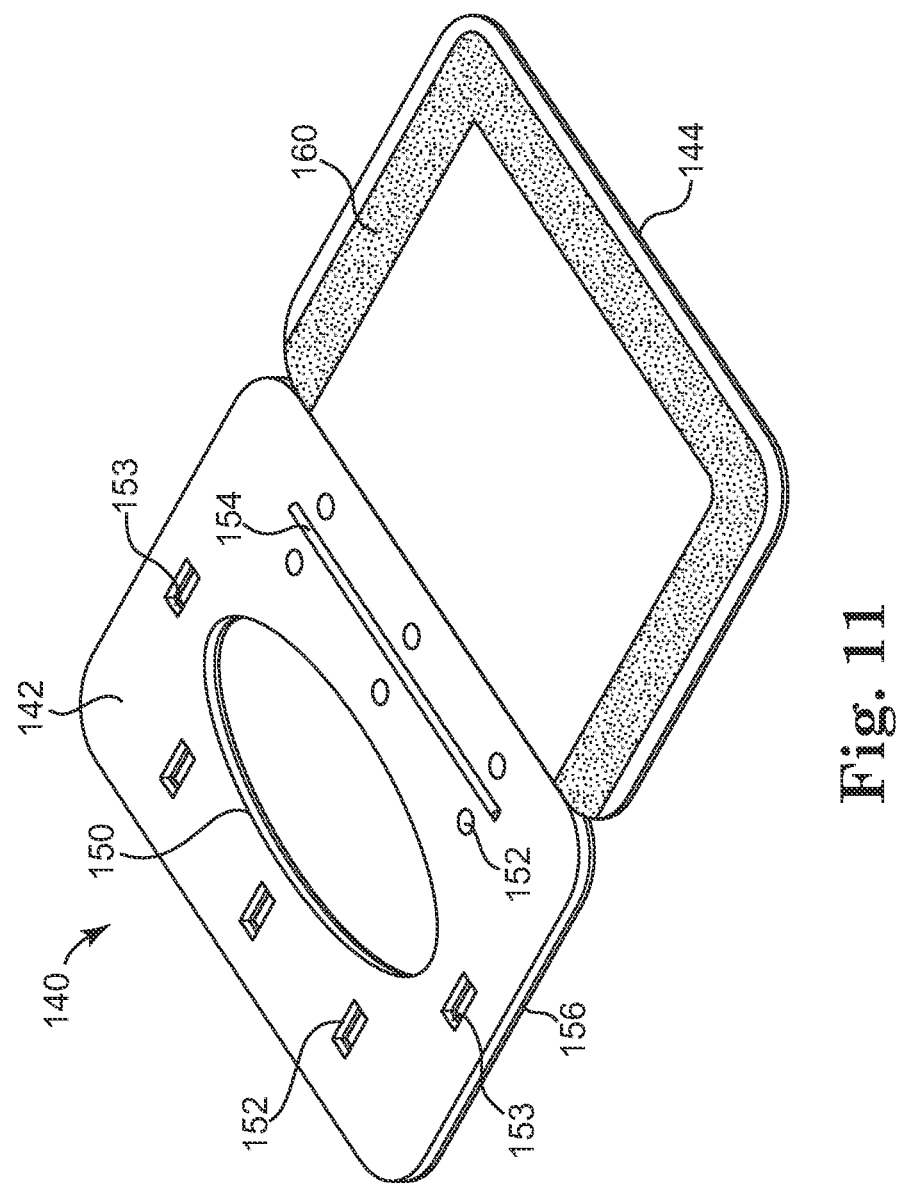

US 9,060,766 B2

SUTURE FIXATION KIT OF PARTS, SYSTEM, AND DEVICE

BACKGROUND

Moles, lesions, and other undesirable tissue growths are commonly removed in a biopsy procedure in which an incision or laceration is created to remove the lesion. The incision or laceration forms a wound that is subsequently repaired, usually with a needle and suture.

After laceration repair, a common problem upon return of the patient to the clinic for suture removal is that the suture has become imbedded in the healed tissue. Removal of such imbedded sutures can possibly reopen the laceration. In addition, suture removal, especially removal of sutures that are imbedded, can be associated with a level of discomfort that is unpleasant to some patients.

SUMMARY

One aspect provides a suture fixation system configured to secure a suture. The system includes a pad and a suture fixation device configured to clamp and retain at least one end of a suture. The pad includes a suture surface opposite a tissue surface and defines an opening formed through the suture and tissue surfaces that is sized to provide a margin around a tissue lesion to be sutured. The suture is employed to stitch the tissue lesion closed, the suture having at least one free end that is held in place by the suture fixation device, and the pad configured to elevate a portion of the suture away from the tissue.

One aspect provides a suture fixation device configured to hold a suture in place after the suture repairs a laceration in a tissue surface. The suture fixation device includes a body having a first segment that is separable from a second segment, the body adapted to be placed on the tissue surface and the first and second segments configured to collapse together to capture at least one free end of the suture between the first and second segments.

One aspect provides a suture fixation kit of parts including a biopsy punch, a pad, and a suture fixation device. The biopsy punch includes a cutting blade extending away from a handle. The handle has a base that defines an incision depth stop for the blade. The biopsy punch defines a window that is sized to ensure a defined margin is formed around a lesion after it is biopsied. The pad defines an opening that is sized to provide a margin around a biopsy incision formed by the rocking biopsy punch. The suture fixation device is configured to clamp and retain at least one end of a suture employed to close the biopsy incision.

BRIEF DESCRIPTION OF THE DRAWINGS

The accompanying drawings are included to provide a further understanding of the disclosure and are incorporated in as a part of this specification. The drawings illustrate example embodiments and together with the description serve to explain principles of the invention. Other embodiments and many of the intended advantages of the embodiments will be readily appreciated as they become better understood by reference to the following detailed description. The elements of the drawings are not necessarily to scale relative to each other. Like reference numerals designate corresponding similar parts.

FIG. 1 is a schematic view of a suture fixation kit of parts including a biopsy punch, a pad, and suture fixation devices according to one embodiment.

FIG. 2 is a top view of the biopsy punch illustrated in FIG. 1.

FIG. 5 is a top view of the punch biopsy adjacent to a skin lesion.

FIG. 9 is a top view of a suture fixation device employed to anchor one end of the suture in closing the laceration according to one embodiment.

FIG. 10 is a top view of the repaired/closed laceration including three suture fixation devices retaining suture ends.

FIG. 11 is a perspective view of a pad suited for use in a suture fixation system according to another embodiment.

DETAILED DESCRIPTION

Figure 3B:
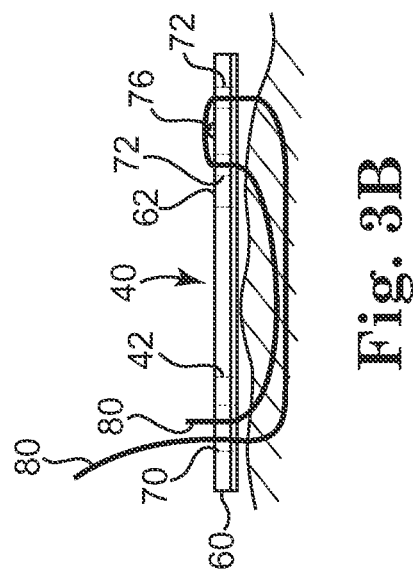
FIG. 3B is a side view of the pad shown in FIG. 3A.

In the following Detailed Description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Lesions, such as moles, are commonly removed from patients. Embodiments provide a suture fixation kit of parts having a biopsy punch sized to excise a specific lesion size and a suture fixation system configured to repair the laceration formed by the biopsy punch.

In one embodiment, the biopsy punch is a rocking biopsy punch configured to remove an ellipse of tissue and provide consistently adequate clean wound margins for even laceration repair. The kits are provided with differently sized biopsy punches to accommodate the size of the lesion to be removed, and each kit includes a system to repair the laceration after it is formed.

Embodiments provide a suture fixation system including a pad defining an opening that is sized to provide a predetermined margin around the laceration to correspond with an elliptical biopsy formed by the rocking biopsy punch, and suture fixation device(s) configured to anchor the free end of the suture as the laceration is stitched closed. In some embodiments, the pad has a structure that elevates the stitch, which prevents the suture from becoming embedded in the tissue as it heals. The suture fixation device(s) anchor the free end of the suture, such that conventional tying of suture ends is no longer needed. The suture fixation device(s) enable quicker and more precise suture closing by doing away with time-consuming knot tying.

Embodiments provide suture fixation device(s) having collapsible segments that enable the device to be "snapped" or quickly attached to anchor the free end of the suture as a stitch is completed.

FIG. 1 is a schematic view of a suture fixation kit of parts 20 according to one embodiment. The kit of parts 20 includes a rocking biopsy punch 22 (shown in a side view) that is configured to create a selectively sized laceration around a tissue lesion to be removed, and a suture fixation system 24 (shown in a top view) configured to repair the laceration created by the rocking biopsy punch 22. In one embodiment, rocking biopsy punch 22 includes a cutting blade 30 extending away from a handle 32. The bottom side of handle 32 provides an incision depth stop for blade 30. Rocking biopsy punch 22 is configured for manual activation in which handle 32 is grasped by fingers of a physician or clinician to rock blade 30 back and forth to create a controlled laceration around a lesion on the skin or other body part, as more fully described below.

Suture fixation system 24 includes a pad 40 that defines a window 42 (or opening 42) that is sized to provide a margin around the laceration created by the rocking biopsy punch 22, and one or more suture fixation devices 44. In one embodiment, opening 42 is disposed around the laceration and pad 40 provides a guide that the physician follows when suturing the laceration created by the rocking biopsy punch 22, which ensures that the suture is evenly spaced from apex-to-apex across the laceration. Different sizes of lesions are addressed with different sizes of openings 42 formed in the pads, such that the kit of parts 20 includes kits sized for small lesions and kits sized for larger lesions. The shape of the opening 42 includes circular shapes and non-circular shapes. Subsequent to suturing the laceration, one of the suture fixation devices 44 is anchored to an end of the suture to hold the suture in place. Other sutures are employed to close the laceration, and additional knotless suture fixation devices 44 are anchored to the free suture ends until the laceration is closed.

FIG. 2 is a top view of rocking biopsy punch 22 (punch 22). In one embodiment, handle 32 includes a grasping surface 50 that defines a window 52 and includes opposing lateral wings 54, 56 and an axial wing 58. Window 52 extends through punch 22 and is configured to provide a viewfinder or window frame that enables the physician to position blade 30 (FIG. 1) around the lesion with a suitable margin, for example a 2 mm margin. The boundary of window 52 is generally aligned with blade 30 such that when a lesion is centered within window 52, blade 30 is also centered around the lesion to provide a margin of unaffected tissue that is suited for suturing. When punch 22 is placed over the lesion, the physician grasps grasping surface 50 such that one or two fingers engage with lateral wing 54, the thumb engages with lateral wing 56, and the index finger engages with axial wing 58. With the punch 22 grasped in this manner, the physician is able to rock the punch 22 relative to an axis that bisects lateral wings 54, 56 to effectuate cutting a clean laceration with blade 30. Thereafter, the lesion is removed and the laceration/wound with the clean margins is suited for repair.

In general, blade 30 (FIG. 1) and window 52 are selectively sized to frame a lesion of a specific size. For example, a lesion observed to have an approximate outside diameter of about 3 mm is accommodated by a punch 22 having an elliptical window 52 that defines a boundary for an elliptical perimeter of blade 30 having a major axis of about 9 mm. Other punches 22 (provided in separate kits 20) are sized to accommodate different sizes of lesions, including lesions having observed diameters ranging from about 3 mm up to about 15 mm. For this range of lesions, the perimeter of window 52 and blade 30 are sized to provide an ellipse having a major axis sized from about 9 mm-40 mm, respectively. Other suitable sizes and other suitable configurations for blade 30 are also acceptable. The elliptical shape cut by blade 30 provides two corners (or apexes) that provide clean edges suited to a linear repair of the incision.

Figure 3A:
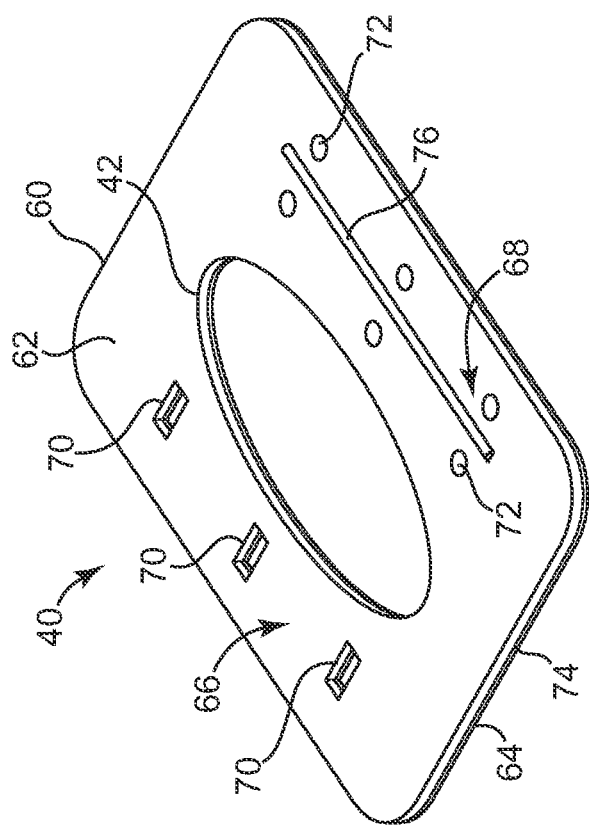
FIG. 3A is a perspective view of the pad illustrated in FIG. 1.

FIG. 3A is a perspective view of pad 40 according to one embodiment. Pad 40 includes a perimeter 60, with the opening 42 formed inside the perimeter 60, and a suture surface 62 opposite a tissue surface 64. The opening 42 extends between the suture surface 62 and the tissue surface 64 to form a first land 66 between opening 42 and perimeter 60 and a second land 68 between opening 42 and perimeter 60. In one embodiment, pad 40 includes holes 70 formed in first land 66 and holes 72 formed in second land 68. Holes 70, 72 provide a guide pattern for a needle that pulls the suture material through pad 40 when closing the laceration framed within opening 42, as best shown in FIG. 10.

In one embodiment, suture surface 62 is a resilient, flexible surface formed of a fabric or plastic material that is configured to impede the suture material from imbedding into the tissue of the patient as the laceration heals. In one embodiment, the suture material is cushioned by suture surface 62 in a manner that separates a portion of the suture away from the patient's tissue to facilitate a pain-free removal of the suture. Suitable material for forming suture surface 62 of pad 40 includes woven fabrics, non-woven fabrics, extruded plastics, or films, for example. In general, suture surface 62 of pad 40 is similar to the material employed in fabricating bandages.

In one embodiment, tissue surface 64 is composed of the same material that forms suture surface 62. In another embodiment, tissue surface 64 includes an adhesive configured to stick to the patient's tissue and position opening 42 around the laceration. In one embodiment, the adhesive is applied as a uniform layer 74 along tissue surface 64. Suitable adhesives include pressure sensitive skin adhesives, acrylates, and acrylate-derived adhesives.

In one embodiment, at least one of the first and second lands 66, 68 includes a prominence 76 extending from suture surface 62. Prominence 76 is provided to ensure that at least a portion of the suture material employed to close the laceration is raised off of pad 40 and away from the patient's tissue to prevent the suture from becoming embedded in the tissue as the laceration heals. Prominence 76 also elevates the suture for eventual snipping, which enables convenient and pain-free removal of the suture after the wound is healed.

FIG. 3B is a side view of pad 40 including one possible example of a suture 80 stitched through pad 40 to close a laceration that is framed within window 42. Other suitable stitch patterns are also acceptable, and are based upon the physician's preference as guided by experience. Suture 80 is stitched through holes 70, 72 of pad 40 and a portion of suture 80 is pulled over to engage with prominence 76. One or more of the free ends of the suture (depending upon the stitch technique) is anchored/clamped by device 44. After the wound heals, suture 80 is snipped near device 44 and the stitch is removed. The portion of the suture 80 resting on prominence 76 is elevated to avoid tissue growing over suture 80 and is also presented for snipping to enable convenient removal of suture 80 from the healed tissue.

Figure 4C:
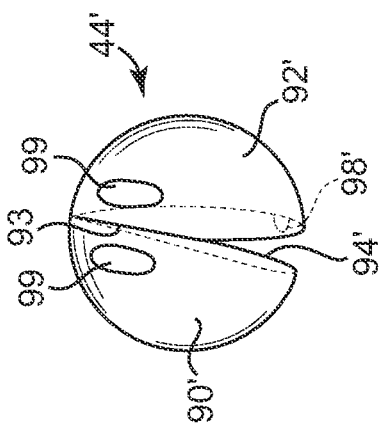
FIG. 4C is a perspective view of a suture fixation device according to another embodiment.
Figure 4B:
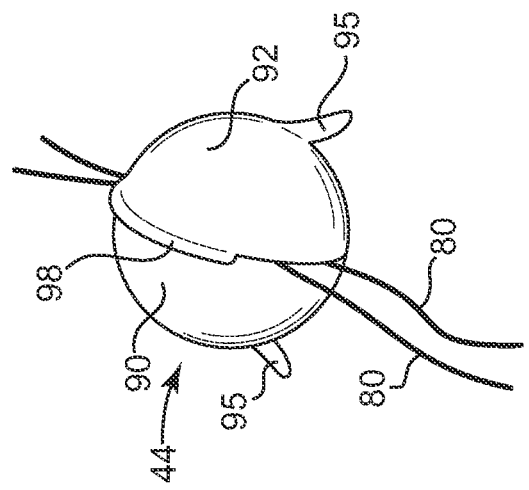
FIGS. 4A and 4B are perspective views of one exemplary form of the suture fixation devices illustrated in FIG. 1.
Figure 4A:
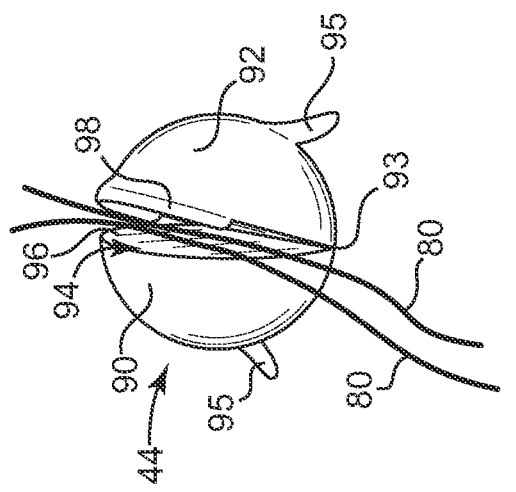

FIGS. 4A and 4B are perspective views of an embodiment of suture fixation device 44 and FIG. 4C is a perspective view of suture fixation device 44'. In one embodiment, suture fixation device 44 (device 44) includes a first segment 90 separated from a second segment 92 by a hinge 93 to define a slot 94 configured to receive the suture 80 (FIG. 3B). Digital control wings 95 extend from segments 90, 92 and are provided to assist in placement of device 44, for example by providing a grasping location for manually controlling suture fixation device 44. In one embodiment, one or both of the interior surfaces of slot 94 includes engagement ridges 96 configured to prevent suture 80 from slipping out of slot 90. A latch 98 is provided to close and hold first segment 90 against second segment 92.

In one embodiment, device 44 is formed of a plastic material and is closed by pinching first segment 90 against second segment 92 until latch 98 engages and holds the two segments together. In one embodiment, device 44 is configured to be pinched closed using finger pressure. Other embodiments provide a higher strength device 44 configured to be pinched closed with the use of a surgical instrument, for example a forceps. In one embodiment, devices 44 are retained in a carousel and selectively dispensed, in a manner similar to a wound closure staple gun.

FIG. 4C illustrates suture fixation device 44' including forceps recesses 99. In one embodiment, each segment 90, 92 includes a forceps recess 99 formed in an exterior surface adjacent to hinge 93. Recess 99 provides a pocket that is sized to receive a pick-ups or handling forceps that can be useful in placing and securing the relatively small devices 44' during a surgical procedure. Suitable forceps include RS 6496 Setting Forceps available from Roboz Surgical Instruments, Inc., Gaithersburg, Md.

First segment 90 is configured to collapse against second segment 92 to capture the free end of suture 80 within slot 94. In one embodiment, segments 90, 92 are elastically deformable segments that are configured to reversibly close slot 94 and capture the free end of suture 80 within slot 94. Upon removal, segments 90, 92 are separated and device 44 is removed from suture 80. In another embodiment, first and second segments 90, 92 are plastically deformable, where segments 90, 92 snap together to irreversibly collapse the slot 94 and bring the segments 90, 92 together. The plastically deformable segments 90, 92 become permanently deformed after deployment around the suture 80, which enables the eventual removal of both the suture 80 and the device 44 clasped onto the suture 80 (after snipping the suture).

In this specification, elastically deformable means forcing a material from a first state into a second state in a manner that the material is able to return to the first state when the force is relieved. In this sense, one embodiment of device 44 provides a spring-like elastically deformable device that is configured to snap over the suture 80 to hold the suture in place and be released (for example by disengaging latch 98) to open device 44 when the laceration is healed.

In this specification, plastically deformable means forcing a material from a first state into a second state in a manner that the material is unable to return to the first state when the force is relieved. The applied force deforms the material beyond its plastic limit. Plastically deforming device 44 thus results in deforming device 44 around suture 80.

FIGS. 5-10 provide views of the kit of parts 20 employed to repair a surgical laceration according to one embodiment.

FIG. 5 is a top view of punch 22 placed adjacent to a skin lesion 100. Skin lesion 100 includes moles or other undesirable growths on skin that are surgically removed in a biopsy procedure.

Figure 6:
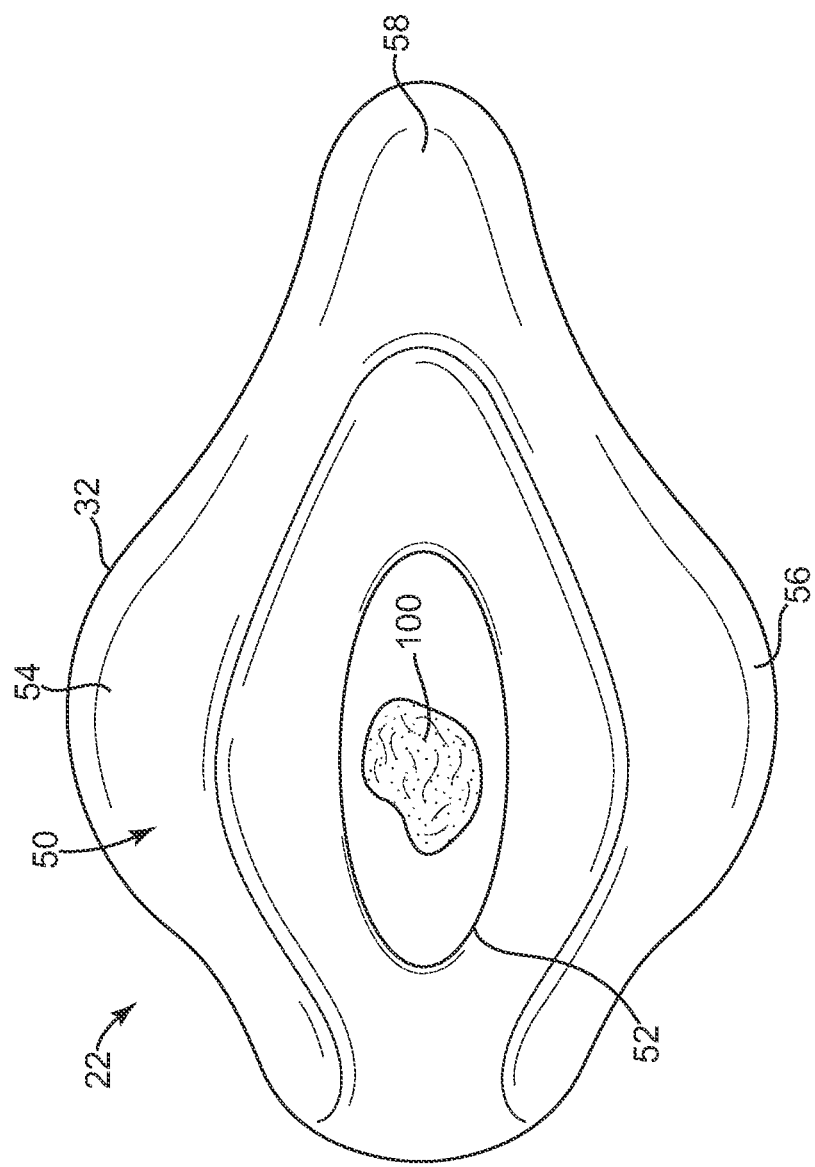
FIG. 6 is a top view of the skin lesion framed in a window of the biopsy punch.

FIG. 6 is a top view of lesion 100 framed within window 52 of punch 22. Punch 22 is suitably positioned to be manually rocked back and forth by manipulating wings 54, 56, 58 to form a surgical laceration 102 around lesion 100. Desirably, punch 22 is selected to provide a margin of unaffected tissue about 2 mm around lesion 100.

Figure 7:
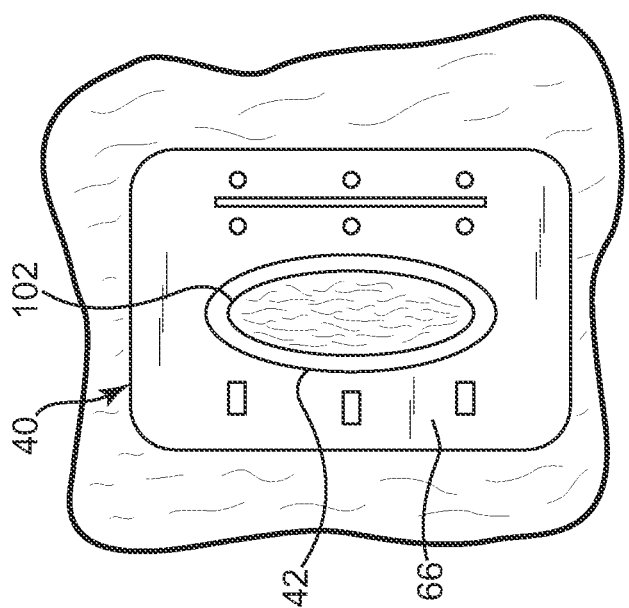
FIG. 7 is a top view of a laceration formed by the biopsy punch and a pad disposed around the laceration according to one embodiment.

FIG. 7 is a top view of the surgical laceration 102 surrounded by pad 40. Opening 42 has been selectively sized to frame and provide a margin around laceration 102.

Figure 8:
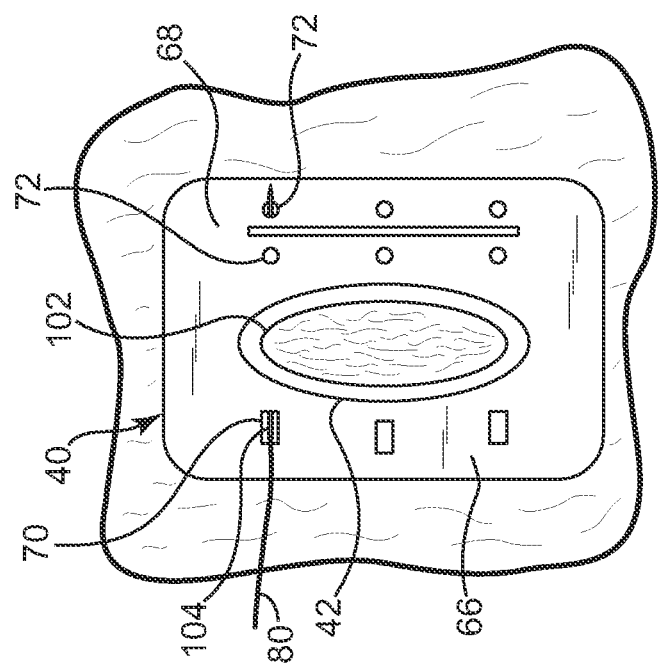
FIG. 8 is a top view of a needle and suture employed to repair the laceration formed by the biopsy punch.

FIG. 8 is a top view of a surgical needle 104 and suture material 80 as employed to close laceration 102. In general, the laceration 102 is closed from apex-to-apex as suture 80 is pulled through the laceration. In this example, needle 104 introduces suture 80 into hole 70 and directs the suture 80 under the laceration 102. The needle 104 is then directed under the distal margin of the laceration 102 and out of the distal hole 72, brought over the prominence 76, and directed back into the proximal hole 72. The suture 80 is then directed under laceration 102 and through the proximal edge of laceration 102, finally exiting hole 70. Suture 80 thus has two sutures ends that are clamped and retained by the suture fixation device 44. Other suitable techniques for suturing laceration 102 are also acceptable.

FIG. 9 is a top view of a first portion of laceration 102 surgically closed by suture 80. Suture 80 is separated from the tissue by land 66 and land 68, and a free end of suture 80 is secured in place (i.e., terminated) without tying a knot by suture fixation device 44. In general, suture fixation device 44 is compatible with any form of suture technique selected by the physician, including, as examples, continuous or interrupted mattress sutures (horizontal or vertical), Cushing sutures, lock-stitch sutures, Lembert sutures, etc.

FIG. 10 is a top view of healed laceration 102. Sutures 80 are removable with a cutting instrument 106. The cutting instrument 106 cuts the suture 80 after the device 44 is lifted with a pick ups (forceps) or with a finger. In addition, at least a portion of suture 80 is maintained off of the skin (in a manner that has minimized the possibility of suture 80 being embedded in the healed wound) and positions suture 80 for easy, pain-free removal. In some embodiments, suture 80 is snipped and pulled out of the healed area by subsequently tugging individually on each fixation device 44.

Embodiments described above provide a suture fixation system including pad 40 and devices 44 that combine to enable closure of a laceration without tying knot(s) in the suture. The suture fixation system also prevents the suture from embedding within the patient's tissue. Other suitable pads and suture fixation devices are described below.

FIG. 11 is a perspective view of a pad 140 according to another embodiment. Pad 140 includes a laceration repair section 142 and a cover section 144. Laceration repair section 142 is employed as described above relative to pad 40 (FIG. 3A), and cover section 144 is provided to be folded over and secured to section 142 to aseptically cover the repaired laceration.

Laceration repair section 142, similar to pad 40, defines an opening 150, suture holes 152, and a prominence 154 configured to elevate the suture off of section 142. In one embodiment, section 142 includes an adhesive layer 156 suited for removably attaching pad 140 to the patient.

In one embodiment, cover section 144 includes an adhesive area 160 configured to removably attach cover section 144 over laceration repair section 142. Adhesive area 160 is suitably provided as one continuous adhesive coating on an interior surface of cover section 144. In other embodiments, adhesive area 160 is provided as two or more discrete sections of adhesive applied to an interior surface of cover section 144. Adhesive area 160 provides a closure mechanism for cover section 144. Other suitable closure mechanisms, including simple tie strings, hook-and-loop fasteners, or individual adhesive tape strips are also acceptable.

In one embodiment, suture holes 152 are not provided and opposing axial suture holes 153 are formed in pad 140 to enable apex-to-apex suturing of a laceration centered in opening 150.

Figure 12:
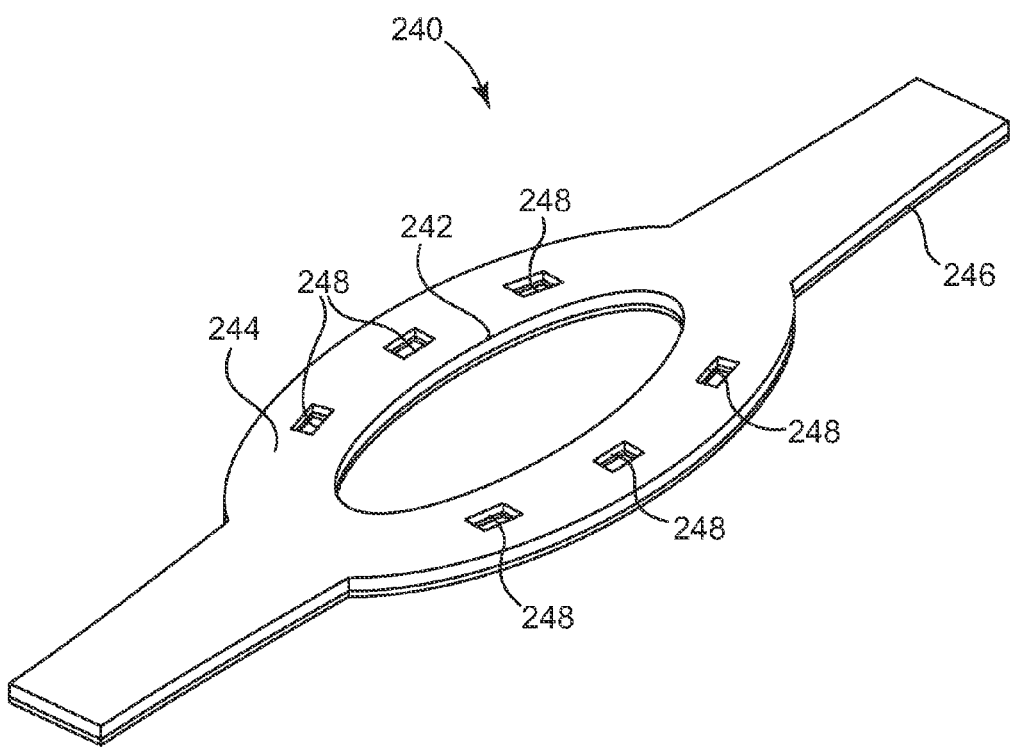
FIG. 12 is a perspective view of a pad according to another embodiment.

FIG. 12 is a perspective view of a pad 240 according to another embodiment. Pad 240 includes an opening 242 extending between a suture surface 244 and a tissue surface 246. In one embodiment, tissue surface 246 is provided as an adhesive layer suited for removably attaching pad 240 to a patient. In one embodiment, opening 242 defines an elliptical perimeter including opposing pairs of holes 248 that are configured to receive strands of the suture that are stitched to close the laceration.

Figure 13:
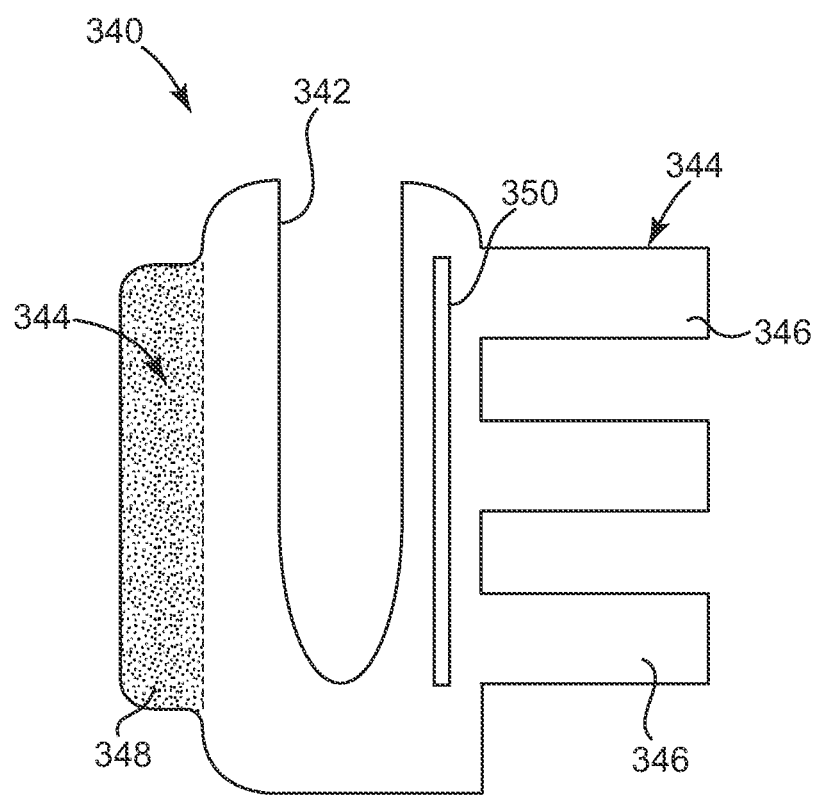
FIG. 13 is a top view of a pad according to another embodiment.

FIG. 13 is a top view of a pad 340 according to another embodiment. Pad 340 includes a non-bounded opening 342 and a closure mechanism 344. In one embodiment, opening 344 is U-shaped or V-shaped, although other shapes for opening 342 are also acceptable. Opening 342 has at least one end that is not closed, which enables the selective and convenient placement of pad 340 around a laceration formed in the tissue. In one embodiment, pad 340 includes holes 70, 72 (FIG. 3A).

In one embodiment, closure mechanism 344 includes strips 346 that are sized to extend over a top of pad 340 to be attached to an adhesive target 348. Strips 346 are sized to reach over opening 342 and prominence 350 and removably attach to adhesive target 348. In one embodiment, strips 346 are elastic to enable the physician to selectively tension the closure mechanism 344 over window 342. Adhesive target 348 includes any suitable adhesive material, for example a pressure sensitive adhesive layer disposed over at least a portion of a top surface of pad 340.

Embodiments described above provide suture fixation devices 44 that clamp about a free end of the suture to anchor the suture in place as the laceration heals. FIGS. 14-17 provide other suitable suture fixation devices.

Figure 14:
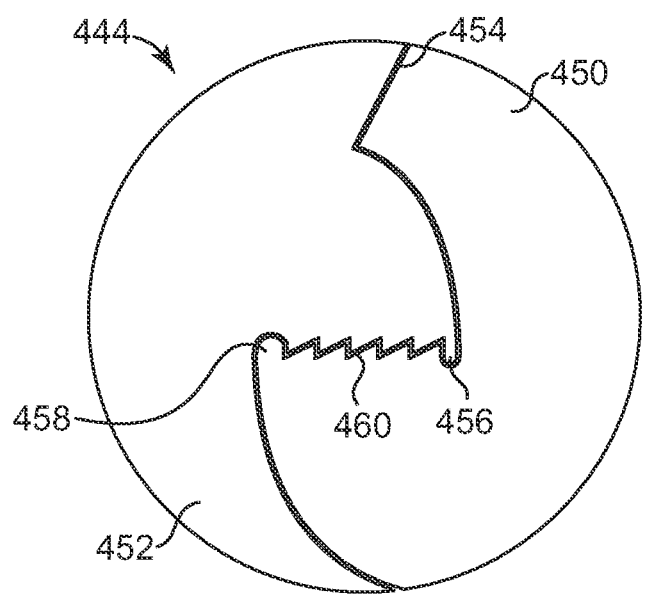
FIG. 14 is a perspective view of a suture fixation device according to another embodiment.

FIG. 14 is a perspective view of a suture fixation 444 device according to another embodiment. Device 444 includes a first section 450 attached to a second section 452 about a hinge 454 that enables first section 450 to close against second section 452 and be retained by latches 456, 458. In one embodiment, when device 444 is closed, first section 450 meshes with second section 452 along a saw tooth mating interface 460 that is configured to clamp against and retain a free end of the suture, consistent with the description provided above.

Figure 15A:
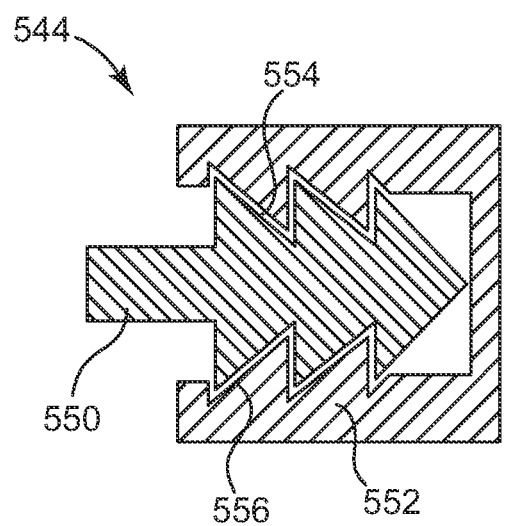
FIG. 15A is a cross-sectional view of a suture fixation device according to another embodiment.

FIG. 15A provides a cross-sectional view of a suture fixation device 544 according to another embodiment. Device 544 includes a first section 550 that is separable from second section 552 such that device 544 is provided in two separate parts. In one embodiment, first section 550 provides a peg defining an exterior articulated surface 554 that is configured to releasably mate with a complementary interior surface 556 of second section 552. In one embodiment, peg 550 is provided as an annular peg that is pressed into a generally circular hole formed by second section 552, such that articulated surface 554 mates with its complementary surface 556 to secure a free end of the suture between section 550 and section 552. In one embodiment, a substantially spherically shaped suture fixation device is provided having opposing separable hemispherical sections, and peg 550 extends from one of the sections to be received by an interior surface 556 of the other of the sections. In this regard, FIG. 15A provides a cross-sectional view of a closure mechanism for a spherically shaped suture fixation device.

Figure 15B:
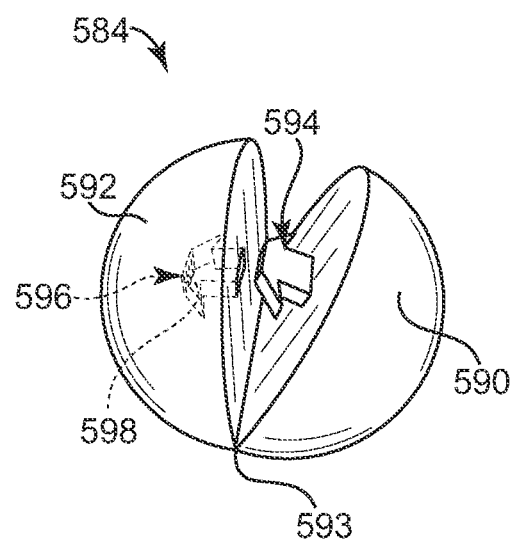
FIG. 15B is a cross-sectional view of a suture fixation device according to another embodiment.

FIG. 15B provides a cross-sectional view of a suture fixation device 584 according to another embodiment. Device 584 includes a first section 590 that is separable from second section 592 along a hinge 593 such that device 584 is provided in two separate parts. In one embodiment, first section 590 provides a peg 594 that is configured to releasably mate with a complementary recess 596 formed in second section 592. In one embodiment, recess 596 includes a serrated surface 598 configured to secure ends of the sutures that are captured between peg 594 and recess 596.

Figure 16:
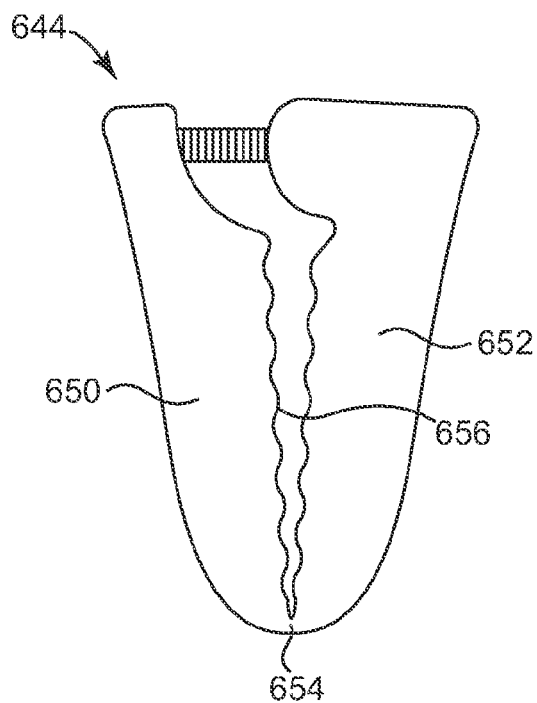
FIG. 16 is a side view of a suture fixation device according to another embodiment.

FIG. 16 is a side view of a suture fixation device 644 according to another embodiment. Device 644 includes a first section 650 attached to a second section 652 about a hinge 654 that enables first section 650 to engage alongside second section 652 and retain the suture material with bite wings 656. In one embodiment, hinge 654 is a living hinge formed by molding a lower portion of section 650 to a lower portion of section 652. In one embodiment, when device 644 is closed, first section 650 shears relative to second section 652 such that the suture material is engaged between the sections 650, 652 and trapped by the shearing action of bite wings 656. In one embodiment, an arm extends from section 650 toward section 652 and is configured to ratchet and engage in a locking manner with a complementary ratcheting structure formed on section 652.

Figure 17:
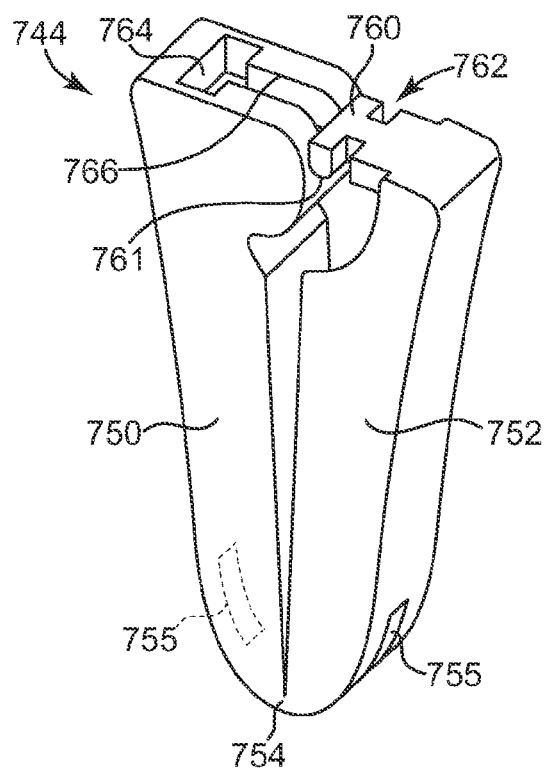
FIG. 17 is a top perspective view of a suture fixation device according to another embodiment.

FIG. 17 is a top perspective view of a suture fixation device 744 according to another embodiment. Device 744 includes a first section 750 attached to a second section 752 about a hinge 754. In one embodiment, each section 750, 752 includes a recess 755 sized to receive a forceps, similar to forceps recess 99 described above in FIG. 4C. Hinge 754 is similar to hinge 654 (FIG. 16). In one embodiment, first section 750 defines a recess 764 formed by a wall 766, and second section 752 includes a prong 760 that is sized to be received by recess 764. Prong 760 defines a projection 761 and a retainer 762. Projection 761 is sized to seat into recess 764 to secure sections 750, 752 together. Retainer 762 is configured to receive suture material. When device 744 is closed, prong 760 engages with recess 764 and projection 761 seats into a well of recess 764 to pinch sections 750, 752 together and trap the suture end(s).

Embodiments provide a suture fixation system including suture fixation device(s) configured to anchor the free end of the suture as the laceration is stitched closed without tying knots, and a pad configured to keep at least a part of the suture from embedding into the tissue as the wound heals. In some embodiments, the pad has a structure that elevates the stitch in the suture, which prevents the suture from becoming embedded in the tissue as it heals. The suture fixation device(s) anchor the free end of the suture, such that conventional tying of suture ends is no longer needed. The suture fixation device(s) enable quicker and more precise suture closing by doing away with time-consuming knot tying. The suture fixation system enables improved wound healing by ensuring that the suture does not embed in the tissue.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific suture fixation devices discussed herein. Therefore, it is intended that this invention be limited only by the claims and the equivalents thereof.

What is claimed is:

1. A suture fixation system configured to secure a suture, the system comprising:
   a pad comprising a suture surface opposite a tissue surface, the pad defining an opening formed through the suture and tissue surfaces that is sized to provide a margin around a tissue incision to be sutured, the suture surface comprises a planar surface;
   a substantially spherically shaped suture fixation device that is separate and distinct from the suture and is configured to clamp and retain at least one free end of the suture adjacent to the suture surface of the pad, and wherein the suture fixation device is configured and sized to retain the at least one free end of the suture directly above a suture hole formed in the pad; and a prominence extending away from the planar surface and positioned between a pair of suture holes formed in the pad and through the planar surface, the prominence spaced apart from the pair of suture holes, and the prominence configured to lift a portion of the suture away from the planar surface;
   wherein the suture is employable to stitch the tissue incision closed, and the pad is configured to elevate a portion of the suture away from the tissue.

2. The system of claim 1, wherein the pad comprises a periphery and the opening comprises a window formed in the pad inside of the periphery.

3. The system of claim 2, wherein the pad comprises a first land extending between the periphery and the window and a second land extending between the periphery and the window on an opposite side of the pad from the first land, the first land formed to define the suture hole on a first side of the opening.

4. The system of claim 3, wherein the second land is formed to define the pair of suture holes on a second side of the opening opposite the first side, the prominence configured to lift a portion of the suture that extends through the pair of suture holes away from the suture surface.

5. The system of claim 1, wherein the tissue surface of the pad comprises adhesive.

6. The system of claim 1, wherein the pad comprises a flap configured to be folded over the suture surface and the opening.

7. The system of claim 1, wherein the suture fixation device comprises a first bead segment separable from a second bead segment, the first and second bead segments configured to clasp together to capture the free end of the suture between the first and second bead segments.

8. The system of claim 7, wherein the first bead segment is formed to include a recess that is sized to receive a peg extending from the second bead segment, the peg insertable into the recess to clasp the first and second bead segments together.

9. The system of claim 7, wherein the first bead segment is separated from the second bead segment by a hinge and each of the first and second bead segments is formed to include a forceps recess adjacent to the hinge.

10. The system of claim 7, wherein each of the first and second bead segments comprise a digital control wing.

11. The system of claim 7, wherein each of the first and second segments comprise a slotted engagement surface, the slotted engagement surfaces configured to mesh together when the first and second segments are pinched together.

12. The system of claim 7, wherein the first and second segments comprise plastically deformable segments.

13. The system of claim 7, wherein the first and second segments comprise elastically deformable segments.

14. The suture fixation system of claim 1, wherein the suture fixation device is configured to clamp and retain the at least one free end of the suture adjacent to the suture surface of the pad on a first side of the opening, and wherein the pair of
   suture holes are formed in the pad on a second side of the opening opposite the first side, the prominence spaced apart from the pair of suture holes, and the prominence configured to lift a portion of the suture that extends through the pair of holes away from the suture surface.

15. A suture fixation system configured to secure a suture, the system comprising:
   a pad comprising a suture surface opposite a tissue surface, the pad defining an opening formed through the suture and tissue surfaces that is configured and sized to be positioned directly over a tissue incision to be sutured and provide a margin around the tissue incision;
   a suture fixation device separate and distinct from the suture and configured to clamp and retain at least one free end of the suture adjacent to the suture surface of the pad on a first side of the opening;
   wherein the suture is employable to stitch the tissue incision closed, and the pad is configured to elevate a portion of the suture away from the tissue; and
   a prominence extending away from the suture surface and positioned between first and second suture holes formed in the pad on a second side of the opening opposite the first side, the prominence spaced apart from the first and second suture holes, and the prominence configured to lift a portion of the suture that extends through the first and second suture holes away from the suture surface.

16. A suture fixation system configured to secure a suture, the system comprising:
   a pad comprising a suture surface opposite a tissue surface, the pad defining an opening formed through the suture and tissue surfaces that is sized to provide a margin around a tissue incision to be sutured;
   a suture fixation device configured to clamp and retain at least one free end of the suture;
   wherein the suture is employable to stitch the tissue incision closed, and the pad is configured to elevate a portion of the suture away from the tissue, and the suture surface comprises a planar surface; and
   a prominence extending away from the planar surface and positioned between suture holes formed in the pad and through the planar surface, the prominence spaced apart from the suture holes, and the prominence configured to lift a portion of the suture away from the planar surface.

* * * * *